United States Patent
Chen et al.

(10) Patent No.: US 11,731,923 B1
(45) Date of Patent: Aug. 22, 2023

(54) METHOD FOR REDUCING CARBON DIOXIDE TO MANUFACTURE MULTI-CARBON HYDROCARBON COMPOUND

(71) Applicant: Chin-Chang Chen, Taichung (TW)

(72) Inventors: Chin-Chang Chen, Taichung (TW); Hung-Lin Chen, Taichung (TW); Fu-Yu Liu, Taichung (TW); Yu-Yun Lin, Taichung (TW)

(73) Assignee: Chin-Chang Chen, Taichung (TW)

( * ) Notice: Subject to any disclaimer, the term of this patent is extended or adjusted under 35 U.S.C. 154(b) by 0 days.

(21) Appl. No.: 18/093,551

(22) Filed: Jan. 5, 2023

(30) Foreign Application Priority Data

Aug. 29, 2022 (TW) .................................. 111132402

(51) Int. Cl.
| | |
|---|---|
| C07C 7/13 | (2006.01) |
| C01B 32/50 | (2017.01) |
| C07C 1/12 | (2006.01) |
| B01D 53/14 | (2006.01) |
| B01D 53/047 | (2006.01) |
| B01D 3/14 | (2006.01) |
| B01D 53/62 | (2006.01) |

(52) U.S. Cl.
CPC .................. *C07C 7/13* (2013.01); *B01D 3/14* (2013.01); *B01D 53/047* (2013.01); *B01D 53/1475* (2013.01); *B01D 53/62* (2013.01); *C01B 32/50* (2017.08); *C07C 1/12* (2013.01); *B01D 2251/304* (2013.01); *B01D 2251/604* (2013.01); *B01D 2257/504* (2013.01); *C01B 2210/0025* (2013.01)

(58) Field of Classification Search
CPC .. C07C 7/13; C07C 1/12; C01B 32/50; C01B 2210/0025; B01D 53/1475; B01D 53/047; B01D 3/14; B01D 53/62
See application file for complete search history.

(56) References Cited

FOREIGN PATENT DOCUMENTS

JP  2013017929 A  * 1/2013  ............. Y02A 50/20

* cited by examiner

*Primary Examiner* — Jafar F Parsa

(57) ABSTRACT

A method for reducing carbon dioxide to manufacture a multi-carbon hydrocarbon compound includes steps as follows. A reduction reaction with separation and purification system is provided, which includes a carbon dioxide absorption tower, a reactor, a gas-liquid separation device, a liquid-phase purification device and a gas-phase purification device. An absorption step is performed, wherein a carbon dioxide gas is absorbed to form a mixed solution. A photo-catalysis step is performed, wherein the mixed solution is reacted with a photocatalyst to form a carbon-based compound. A separation step is performed, wherein the carbon-based compound is separated to form a liquid-phase mixture and a gas-phase mixture. A liquid-phase purification step is performed, wherein the liquid-phase mixture is purified. A gas-phase purification step is performed, wherein the gas-phase mixture is separated and purified to form a multi-carbon hydrocarbon compound.

10 Claims, 4 Drawing Sheets

METHOD FOR REDUCING CARBON DIOXIDE TO MANUFACTURE MULTI-CARBON HYDROCARBON COMPOUND

RELATED APPLICATIONS

This application claims priority to Taiwan Application Serial Number 111132402, filed Aug. 29, 2022, which is herein incorporated by reference.

BACKGROUND

Technical Field

The present disclosure relates to a method for reducing carbon dioxide. More particularly, the present disclosure relates to a method for reducing carbon dioxide to manufacture a multi-carbon hydrocarbon compound.

Description of Related Art

The fossil fuel is the most common power source at present, and occupies an important position in the industrial development, the transportation and the agricultural development. However, the use of the fossil fuel will emit the large amount of the carbon dioxide, causing the environment problems such as the greenhouse effect and the air pollution. In order to achieve the sustainable development of the environment, how to reduce the emissions of the carbon dioxide and the energy regeneration is an important issue today.

At present, the method for reducing the emission of the carbon dioxide is to use the high-efficiency power generation system, but its energy consumption is large and needs the high-cost operation, which does not meet the economic benefits. In order to save the costs, reduce the energy consumption and protect the environment, the photocatalytic reduction of the carbon dioxide is the main research technology, which uses the sunlight as the energy source, and does not produce the additional carbon dioxide when using the photocatalysts for the reaction. However, this method for reducing the carbon dioxide will produce the variety of organics with different properties.

Therefore, how to design a process for reducing the carbon dioxide, and separate and purify the generated organics to meet the economic benefits is the goal of the relevant industry.

SUMMARY

According to one aspect of the present disclosure, a method for reducing carbon dioxide to manufacture a multi-carbon hydrocarbon compound includes steps as follows. A reduction reaction with separation and purification system is provided, which includes a carbon dioxide absorption tower, a reactor, a gas-liquid separation device, a liquid-phase purification device and a gas-phase purification device. The carbon dioxide absorption tower has an absorbent. The reactor is communicated to a liquid outlet of the carbon dioxide absorption tower and has a photocatalyst. The gas-liquid separation device is communicated with the reactor, and the gas-liquid separation device is connected with a liquid-phase tank and a gas-phase tank by a first flow path and a second flow path, respectively. The liquid-phase purification device is communicated with the liquid-phase tank. The gas-phase purification device includes a washing tower and at least one separation column set, wherein the washing tower is communicated with the gas-phase tank, and the at least one separation column set is connected with the washing tower. An absorption step is performed, wherein a carbon dioxide gas is performed a carbon dioxide absorption treatment by the absorbent in the carbon dioxide absorption tower to form a mixed solution. A photocatalysis step is performed, wherein the mixed solution is reacted with the photocatalyst under an irradiation of a light source in the reactor to form a carbon-based compound. A separation step is performed, wherein the carbon-based compound is separated by the gas-liquid separation device to form a liquid-phase mixture and a gas-phase mixture, which are stored in the liquid-phase tank and the gas-phase tank, respectively. A liquid-phase purification step is performed, wherein the liquid-phase mixture is filtered and dried in the liquid-phase purification device to purify the liquid-phase mixture. A gas-phase purification step is performed, wherein the gas-phase mixture is washed by the washing tower, and separated and purified the gas-phase mixture in the at least one separation column set by a pressure swing adsorption method in the gas-phase purification device to form a multi-carbon hydrocarbon compound.

BRIEF DESCRIPTION OF THE DRAWINGS

The present disclosure can be more fully understood by reading the following detailed description of the embodiment, with reference made to the accompanying drawings as follows.

DETAILED DESCRIPTION

Figure 1:
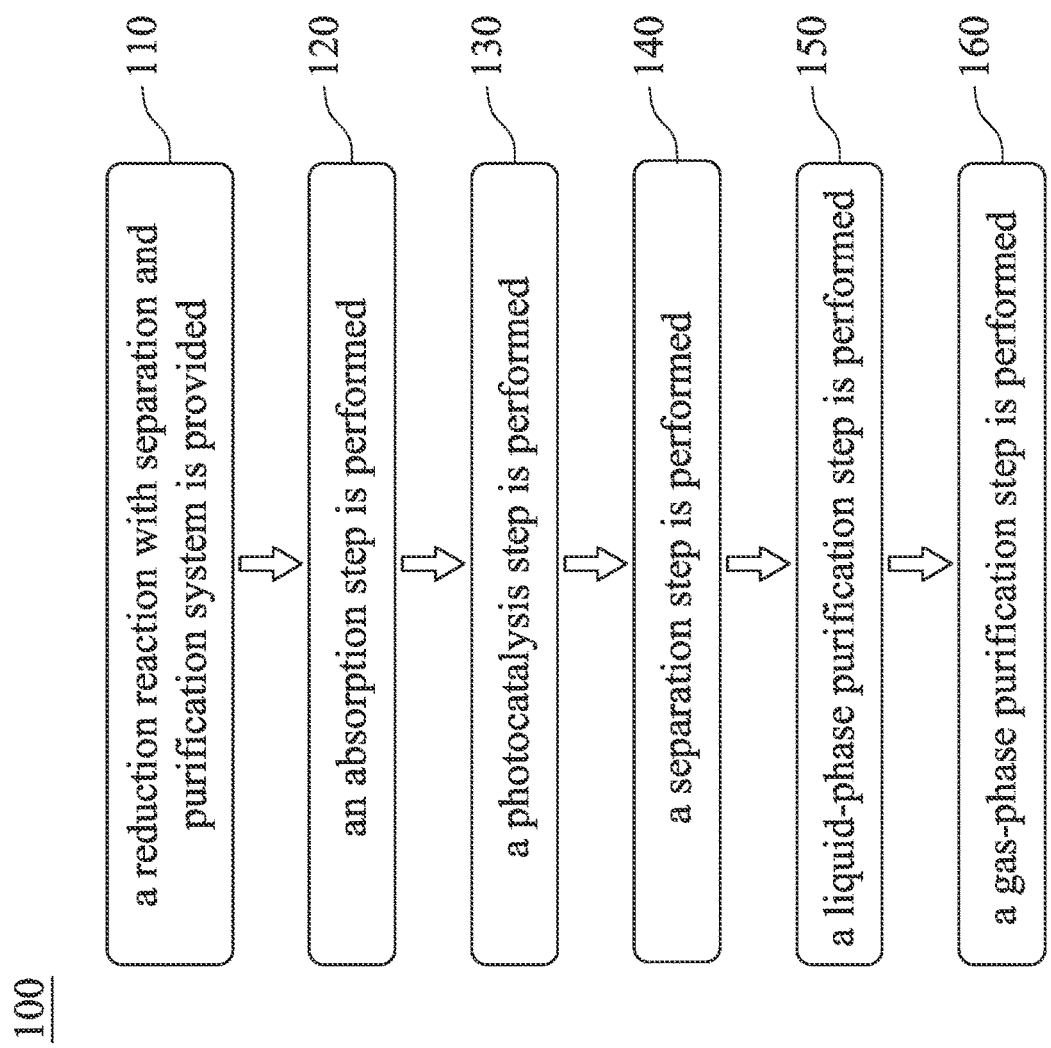
FIG. 1 is a flow chart of a method for reducing carbon dioxide to manufacture a multi-carbon hydrocarbon compound according to one embodiment of the present disclosure.

The embodiments of the present disclosure will be described below by referring the figures. For the clarity, many practical details will be explained in the following description. However, the readers should realize that these practical details are not limited to the present disclosure. That is, in some embodiments of the present disclosure, the practical details are not necessary. In addition, in order to simplify the figures, some of the conventional structures and elements will be shown in the figures with simplified schematic; and the repeated elements will be shown by the same reference numerals.

Figure 2:
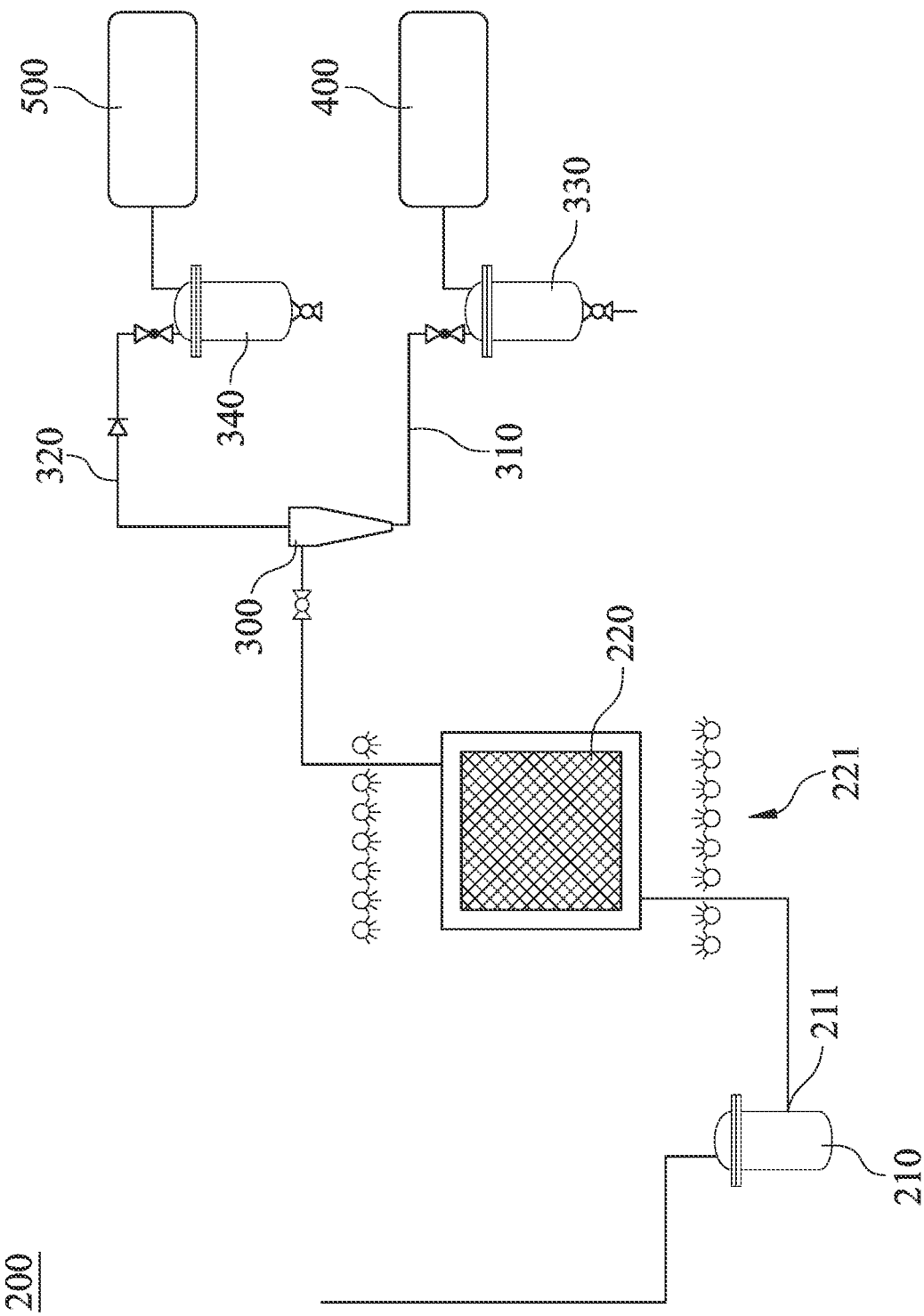
FIG. 2 is a schematic diagram of a reduction reaction with separation and purification system of the method for reducing carbon dioxide to manufacture the multi-carbon hydrocarbon compound as shown in FIG. 1.

Reference is made to FIG. 1 and FIG. 2, wherein FIG. 1 is a flow chart of a method for reducing carbon dioxide to manufacture a multi-carbon hydrocarbon compound 100 according to one embodiment of the present disclosure. FIG. 2 is a schematic diagram of a reduction reaction with separation and purification system 200 of the method for reducing carbon dioxide to manufacture the multi-carbon hydrocarbon compound 100 as shown in FIG. 1. In FIG. 1, the method for reducing carbon dioxide to manufacture the multi-carbon hydrocarbon compound 100 includes a step 110, a step 120, a step 130, a step 140, a step 150 and a step 160.

In the step 110, a reduction reaction with separation and purification system 200 is provided, as shown in FIG. 2, the reduction reaction with separation and purification system 200 includes a carbon dioxide absorption tower 210, a reactor 220, a gas-liquid separation device 300, a liquid-phase purification device 400, and a gas-phase purification device 500. The carbon dioxide absorption tower 210 has an absorbent. The reactor 220 is communicated to a liquid outlet 211 of the carbon dioxide absorption tower 210 and has a photocatalyst. The gas-liquid separation device 300 is communicated with the reactor 220, and connected with a liquid-phase tank 330 and a gas-phase tank 340 by a first flow path 310 and a second flow path 320, respectively. The liquid-phase purification device 400 is communicated with the liquid-phase tank 330, and the gas-phase purification device 500 is communicated with the gas-phase tank 340.

The details of each steps of the method for reducing carbon dioxide to manufacture the multi-carbon hydrocarbon compound 100 will be described in the following, and the related process systems are respectively matched.

In the step 120, an absorption step is performed, wherein a carbon dioxide gas is performed a carbon dioxide absorption treatment by the absorbent in the carbon dioxide absorption tower 210 to form a mixed solution. Specifically, the absorbent of the present disclosure is a sodium hydroxide, and the carbon dioxide gas is chemically absorbed in the carbon dioxide absorption tower 210 and stored in the sodium hydroxide solution in form of a carbonate state. This step can fully absorb the carbon dioxide, avoid the unnecessary losses, and can eliminate the pollution of foreign gas to avoid the interference of the unnecessary gases (such as nitrogen) on the reaction.

In the step 130, a photocatalysis step is performed, wherein the mixed solution is reacted with the photocatalyst under an irradiation of a light source 221 in the reactor 220 to form a carbon-based compound. Specifically, the mixed solution containing the carbon dioxide and the sodium hydroxide is sent to the reactor 220, and is irradiated by the light source 221 in the liquid phase to perform the photocatalytic reaction with the photocatalyst. At this time, the carbon dioxide is catalytically reduced to the carbon-based compound.

In detail, the photocatalyst of the present disclosure can include but not limited to a selenium-based compound, a tellurium-based compound, an arsenic-based compound or a compound represented by formula (i), formula (ii), formula (iii), formula (iv) or formula (v):

| | |
|---|---|
| $M^1A^1X$ | formula (i), |
| $M^2BiO_2X$ | formula (ii), |
| BiOX/BiOY | formula (iii), |
| BiOX/BiOY/BiOZ | formula (iv), |
| $M^3A^2O$ | formula (v), | wherein $M^1$ is bismuth, antimony, gallium or indium, $M^2$ is lead, calcium, strontium, barium, copper or iron, and $M^3$ is lithium, sodium, or potassium. $A^1$ is oxygen, sulfur, selenium or tellurium, and $A^2$ is titanium, vanadium, chromium, manganese, iron, cobalt, nickel, zirconium, niobium, tantalum, molybdenum or tungsten. X, Y, Z are fluorine, chlorine, bromine or iodine. Furthermore, the photocatalyst of the present disclosure can further include a composite of the selenium-based compound, the tellurium-based compound, the arsenic-based compound or the compound represented by formula (i), formula (ii), formula (iii), formula (iv) or formula (v) with a two-dimensional structural material. The two-dimensional structure material can be but not limited to a graphitic carbon nitride (g-$C_3N_4$), a graphene oxide (GO), a bismuth oxyhalide-based compound (BiOX), a sulfur-doped graphitic carbon nitride (S—$C_3N_4$), a carbon nanotube (CNT) or a graphene (GR). Therefore, the efficiency of the photocatalytic reduction can be enhanced by synthesizing various photocatalysts or composite photocatalysts to promote the separation of electron-hole.

In the step 140, a separation step is performed, wherein the carbon-based compound is separated by the gas-liquid separation device 300 to form a liquid-phase mixture and a gas-phase mixture, which are stored in the liquid-phase tank 330 and the gas-phase tank 340, respectively. Specifically, after the photocatalytic reduction, the carbon-based compound can include the methane, the formaldehyde, the methanol and the formic acid, etc., and sent to the liquid-phase tank 330 and the gas-phase tank 340 for collecting by the simple gas-liquid separation for the subsequent processing procedure. Furthermore, both of the liquid-phase tank 330 and the gas-phase tank 340 can be provided with a reflux device as a tool for adjusting the reaction conditions to define the reaction residence time, the gas-liquid ratio and the catalyst performance, but the present disclosure is not limited thereto.

Figure 3:
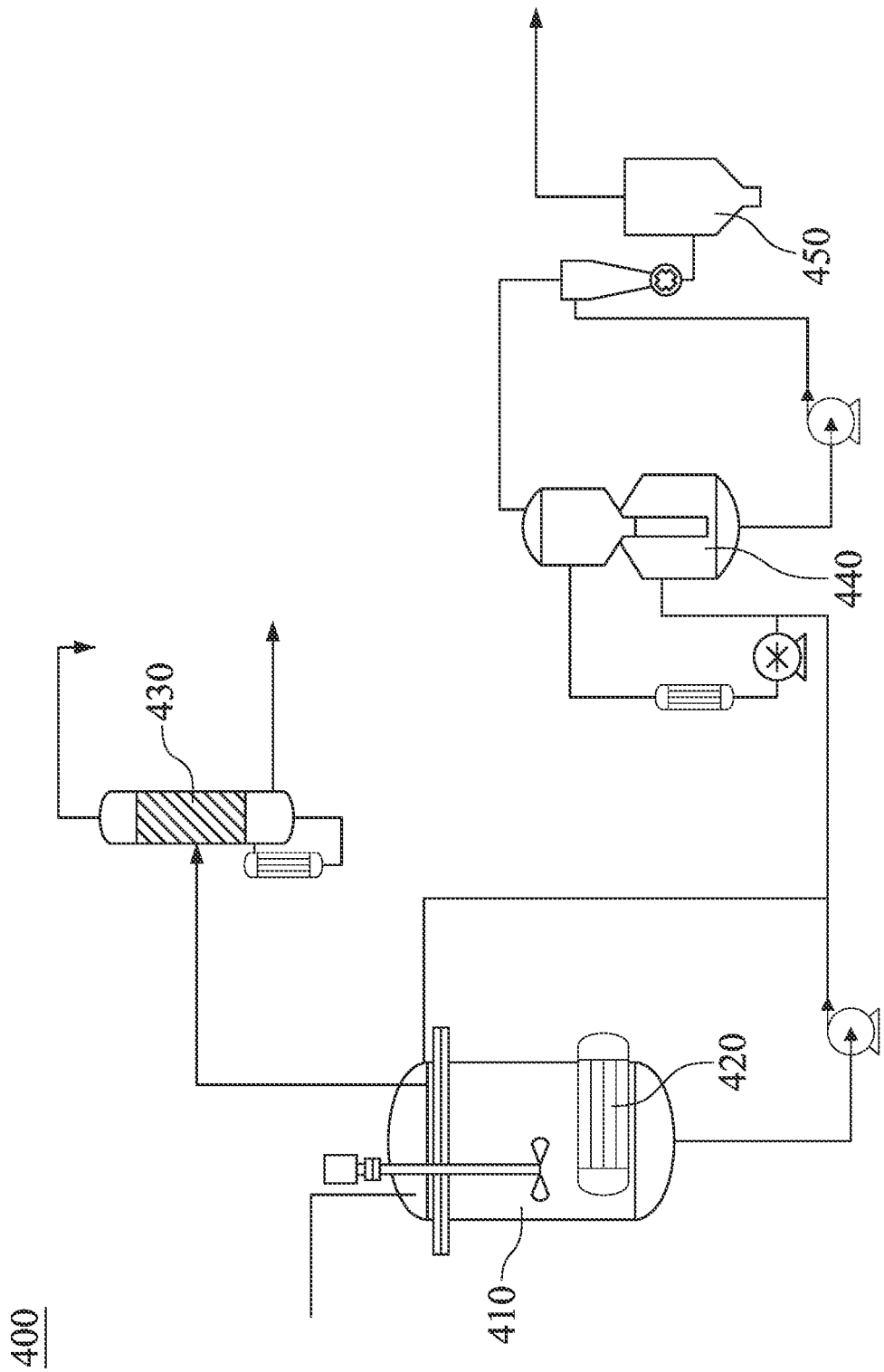
FIG. 3 is a schematic diagram of the liquid-phase purification device of the reduction reaction with separation and purification system as shown in FIG. 2.

In the step 150, a liquid-phase purification step is performed, wherein the liquid-phase mixture is filtered and dried in the liquid-phase purification device 400 to purify the liquid-phase mixture. Reference is made to FIG. 3, which is a schematic diagram of the liquid-phase purification device 400 of the reduction reaction with separation and purification system 200 as shown in FIG. 2. The liquid-phase purification device 400 includes a stirring tank 410, a heater 420, a distillation column 430, a filter 440 and an oven 450.

Specifically, the liquid-phase mixture contains the incomplete reaction carbon dioxide and the possible components of the by-products such as the formaldehyde, the methanol, the formic acid, the moisture and the sodium hydroxide. Under the alkaline condition, the formic acid is not easy to exist independently, and it will form the sodium formate salt with the sodium hydroxide solution and dissolve in the solution. Furthermore, the formaldehyde is easy to form the sodium formate and the methanol under the condition of high pH value. When the liquid-phase mixture is sent from the liquid-phase tank 330 to the stirring tank 410, the heater 420 will be used for heating, so that the methanol, the carbon dioxide and the water vapor which are sensitive to the temperature condition will escape, and sent to the distillation column 430 arranged at the top of the stirring tank 410 for the separation. The methanol can be collected at the top of the tower, and the carbon dioxide can be refluxed to the reaction zone to re-react the photocatalytic reaction. Furthermore, when the temperature of the stirring tank 410 is lowered, the solubility of the sodium formate will be reduced, so that the sodium formate crystallize is precipitated, and then the sodium formate crystallize is passed through the filter 440 to separate the sodium formate. The sodium hydroxide solution that has been reduced by the sodium formate can be refluxed to the reaction zone to re-participate in the absorption of the carbon dioxide gas and the photocatalytic reaction. Moreover, the filtered sodium formate with the cake-shaped is sent to the oven 450 to perform the purification. If the methanol or the sodium hydroxide is remained on the surface of the sodium formate too much, it can be cleaned with the ethanol.

Figure 4:
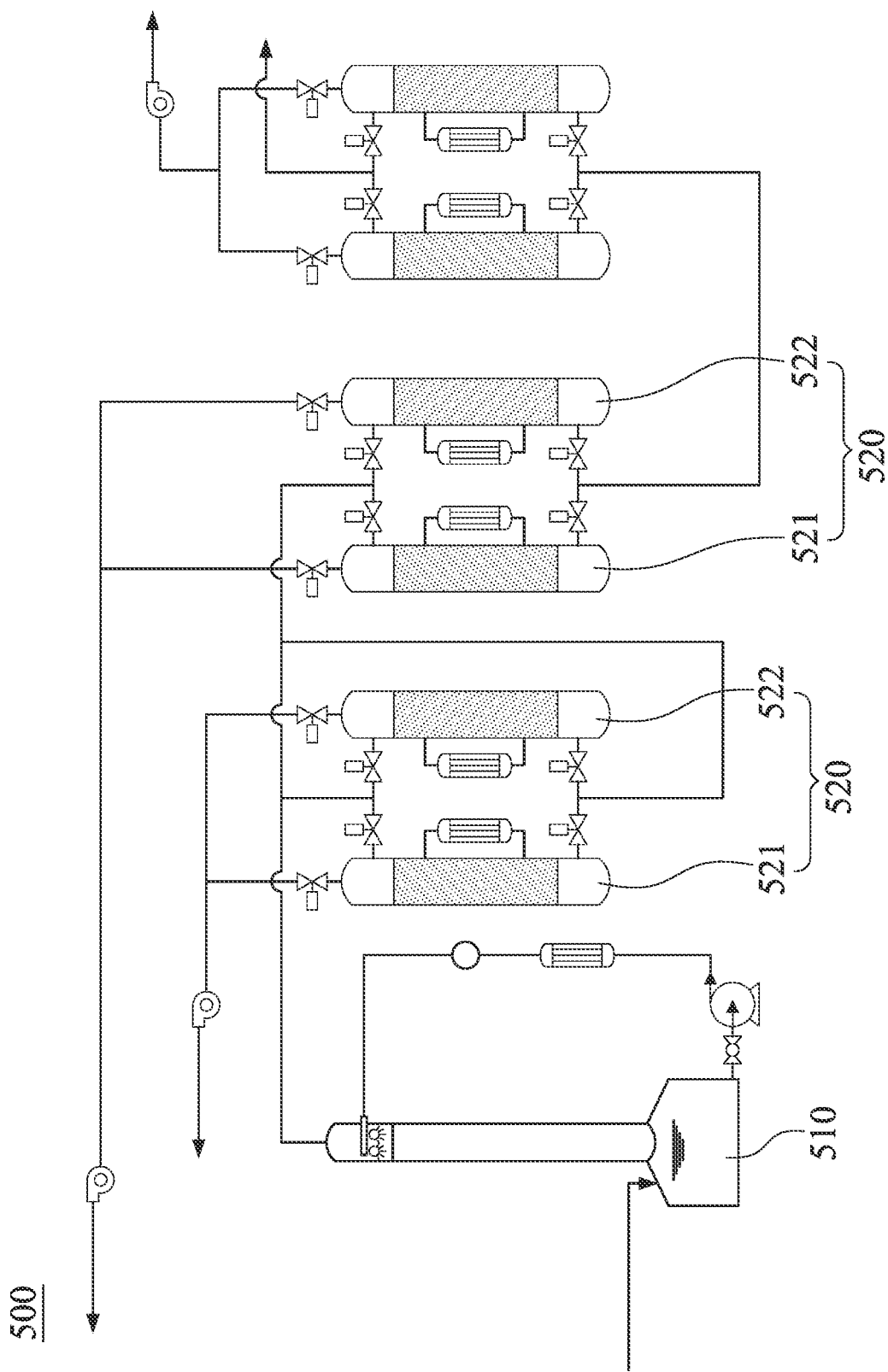
FIG. 4 is a schematic diagram of the gas-phase purification device of the reduction reaction with separation and purification system as shown in FIG. 2.

In the step 160, a gas-phase purification step is performed, wherein the gas-phase mixture is separated and purified by a pressure swing adsorption method (PSA) in the gas-phase purification device 500 to form a multi-carbon hydrocarbon compound. Reference is made to FIG. 4, which is a schematic diagram of the gas-phase purification device 500 of the reduction reaction with separation and purification system 200 as shown in FIG. 2. The gas-phase purification device 500 includes a washing tower 510 and at least one separation column set 520. The washing tower 510 is communicated with the gas-phase tank 340, and the separation column set 520 is connected with the washing tower 510.

Specifically, the gas-phase mixture may contain the components such as the methanol, the methane, the carbon monoxide, the formaldehyde, the formic acid, the incomplete reaction carbon dioxide and the oxygen formed from the moisture in the photocatalytic reaction. The gas-phase mixture is sent from the gas-phase tank 340 to the washing tower 510, and washed by the washing tower 510. The washing tower 510 contains the sodium hydroxide to remove the formic acid and the formaldehyde under the alkaline condition, and the carbon dioxide gas released from the incomplete reaction can also be washed, absorbed at the same time and recycled to the reaction zone.

Then, the gases washed by the sodium hydroxide are left with the methane, the carbon monoxide, the methanol, the carbon dioxide and the small amount of the impurities, and the different gases are separated and purified by using the separation column set 520 and the pressure swing adsorption technology. In detail, a number of the separation column set 520 of the present disclosure can be three, and not limited thereto. Furthermore, an adsorbent material contained in the separation column set 520 can be but not limited to a zeolite, a silica gel, an activated carbon, an activated oxidation aluminum or a 4 Å molecular sieve. The substances that can be adsorbed by each adsorbent material are different, and the desired adsorbent material can be selected according to the different characteristics of the gas. Moreover, each of the separation column set 520 includes an adsorption column 521 and a desorption column 522, and the adsorption is performed at the normal temperature and the high pressure. A certain gas in the gas-phase mixture is adsorbed, and then desorbed by vacuuming. The gas-phase mixture can be separated and purified by repeating the operation. The pressure swing adsorption technology is well known in the art and will not be described herein.

In addition, after the gas-phase purification step, a detection step can be further included, wherein a detection device (not shown) is connected to the gas-phase purification device 500 to measure a production of the multi-carbon hydrocarbon compound, and the detection device is a gas chromatography. In detail, the detection device is used to measure the multi-carbon hydrocarbon compound to obtain the chromatographic data of the reaction at each time point, and analyze the types and the production of the multi-carbon hydrocarbon.

The present disclosure will be further exemplified by the following specific embodiments so as to facilitate utilizing and practicing the present disclosure completely by the people skilled in the art without over-interpreting and over-experimenting. However, the readers should understand that the present disclosure should not be limited to these practical details thereof, that is, these practical details are used to describe how to implement the materials and methods of the present disclosure and are not necessary.

Example

<Reducing Carbon Dioxide to Manufacture Multi-Carbon Hydrocarbon Compound>

The method for reducing carbon dioxide to manufacture the multi-carbon hydrocarbon compound 100 of the present disclosure is performed as shown in FIG. 1. Specifically, the carbon dioxide gas is absorbed by the alkaline solution of the sodium hydroxide first, then 0.1 g of the photocatalyst is added, and the carbon dioxide is reduced to the carbon-based compound under the irradiation of the ultraviolet light or the visible light. Next, the reduced carbon-based compound is performed the gas-liquid separation, and the gas-phase mixture and the liquid-phase mixture are separated and purified respectively. Finally, the gas chromatography is used to measure the production of the separated and purified gas-phase substance.

In detail, the photocatalysts used in the present disclosure are shown in Table 1.

TABLE 1

| | | |
|---|---|---|
| Photocatalyst (i) | Example 1 | BiSeI/g-$C_3N_4$ |
| | Example 2 | BiSeCl/GO |
| | Example 3 | BiTeI/GR |
| | Example 4 | SbOBr |
| Photocatalyst (ii) | Example 5 | $PbBiO_2I$/GO |
| | Example 6 | $PbBiO_2Br$ |
| | Example 7 | $PbBiO_2Cl$ |
| | Example 8 | $PbBiO_2Br$/g-$C_3N_4$ |
| Photocatalyst (iii) | Example 9 | $Bi_{50}O_{59}F_{32}$/BiOI/GO |
| Photocatalyst (iv) | Example 10 | BiOI/BiOBr/$Bi_4O_5Br_2$ |
| Photocatalyst (v) | Example 11 | $KVO_3$ |
| | Example 12 | $Na_3NbO_4$ |
| | Example 13 | $Li_2MoO_4$ |
| | Example 14 | $K_2Fe_2O_4$/g-$C_3N_4$ |
| Selenium-based photocatalyst | Example 15 | $Ga_2Se_3$ |
| | Example 16 | $CsYZnSe_3$ |
| Tellurium-based photocatalyst | Example 17 | $Sr(InTe_2)_2$ |
| | Example 18 | $RbAuTe_2$ |
| Arsenic-based photocatalyst | Example 19 | $BeSiAs_2$ |
| | Example 20 | $MgSiAs_2$ |

<Multi-Carbon Hydrocarbon Compound Analysis>

In the gas-phase purification step of the present disclosure, the four separation column sets are used to separate and purify the various hydrocarbon compounds. The zeolite is used to separate and purify the ethylene, the activated carbon is used to separate and purify the methane, the ethane, the propane, the butane and the pentane, the 4 Å molecular sieve is used to separate and purify the propylene, the activated oxidation aluminum is used to separate and purify the acetylene. Furthermore, the above-mentioned hydrocarbon compounds are analyzed by the gas chromatography, and the measurement time point (hr), the concentration (ppm) and the yield (μmol/g/h) thereof are listed in Table 2.

TABLE 2

| | | Example 1 | Example 2 | Example 3 | Example 4 |
|---|---|---|---|---|---|
| Measurement time point | | 144 | 144 | 196 | 72 |
| Concentration (Yield) | $CH_4$ | 600 (0.51) | 876 (0.74) | 715 (0.44) | 453 (0.77) |
| | $C_2H_6$ | 165 (0.14) | 86 (0.07) | 96 (0.06) | 67 (0.11) |
| | $C_2H_4$ | N/A | 180 (0.15) | N/A | 86 (0.15) |
| | $C_2H_2$ | N/A | N/A | N/A | N/A |

TABLE 2-continued

|  |  | Example 1 | Example 2 | Example 3 | Example 4 |
|---|---|---|---|---|---|
|  | $C_3H_8$ | 35 (0.03) | 30 (0.02) | 51 (0.03) | 60 (0.10) |
|  | $C_3H_6$ | N/A | 10 (0.08) | N/A | 26 (0.04) |
|  | $C_4H_{10}$ | 10 (0.01) | 11 (0.01) | 24 (0.02) | 18 (0.03) |
|  | $C_5H_{12}$ | N/A | 11 (0.01) | 8 (0.01) | 15 (0.03) |
|  |  | Example 5 | Example 6 | Example 7 | Example 8 |
| Measurement time point |  | 144 | 120 | 120 | 120 |
| Concentration | $CH_4$ | 123 (0.10) | 562 (0.57) | 1110 (1.13) | 253 (0.26) |
| (Yield) | $C_2H_6$ | 9 (0.01) | 137 (0.14) | 637 (0.65) | 37 (0.04) |
|  | $C_2H_4$ | 13 (0.01) | 61 (0.06) | 76 (0.08) | 26 (0.03) |
|  | $C_2H_2$ | N/A | N/A | N/A | N/A |
|  | $C_3H_8$ | 12 (0.01) | 67 (0.07) | 216 (0.22) | 30 (0.03) |
|  | $C_3H_6$ | N/A | 11 (0.01) | 31 (0.03) | 12 (0.01) |
|  | $C_4H_{10}$ | 5 (0.04) | 29 (0.03) | 88 (0.09) | 10 (0.01) |
|  | $C_5H_{12}$ | 5 (0.04) | 10 (0.01) | 23 (0.02) | 5 (0.01) |
|  |  | Example 9 | Example 10 | Example 11 | Example 12 |
| Measurement time point |  | 144 | 144 | 144 | 144 |
| Concentration | $CH_4$ | 876 (0.74) | 90 (0.07) | 656 (0.56) | 281 (0.24) |
| (Yield) | $C_2H_6$ | 86 (0.07) | 25 (0.08) | 286 (0.24) | 57 (0.05) |
|  | $C_2H_4$ | 180 (0.15) | 6 (0.05) | 54 (0.05) | 12 (0.01) |
|  | $C_2H_2$ | N/A | N/A | 15 (0.01) | N/A |
|  | $C_3H_8$ | 30 (0.02) | 5 (0.02) | 76 (0.06) | 19 (0.02) |
|  | $C_3H_6$ | 10 (0.08) | N/A | N/A | N/A |
|  | $C_4H_{10}$ | 11 (0.01) | N/A | 8 (0.01) | N/A |
|  | $C_5H_{12}$ | 11 (0.01) | N/A | N/A | N/A |
|  |  | Example 13 | Example 14 | Example 15 | Example 16 |
| Measurement time point |  | 144 | 144 | 144 | 120 |
| Concentration | $CH_4$ | 537 (0.46) | 650 (0.55) | 201 (0.17) | 1167 (1.19) |
| (Yield) | $C_2H_6$ | 150 (0.13) | 60 (0.05) | 68 (0.06) | 711 (0.73) |
|  | $C_2H_4$ | 32 (0.03) | 67 (0.05) | 36 (0.03) | 134 (0.14) |
|  | $C_2H_2$ | N/A | 15 (0.01) | N/A | N/A |
|  | $C_3H_8$ | 64 (0.05) | N/A | 31 (0.03) | 488 (0.50) |
|  | $C_3H_6$ | N/A | 22 (0.01) | 23 (0.02) | 56 (0.57) |
|  | $C_4H_{10}$ | 14 (0.01) | 15 (0.01) | 17 (0.01) | 263 (0.27) |
|  | $C_5H_{12}$ | N/A | N/A | 9 (0.01) | 55 (0.06) |
|  |  | Example 17 | Example 18 | Example 19 | Example 20 |
| Measurement time point |  | 168 | 168 | 168 | 144 |
| Concentration | $CH_4$ | 1359 (0.99) | 1043 (0.76) | 520 (0.38) | 420 (0.36) |
| (Yield) | $C_2H_6$ | 689 (0.50) | 421 (0.31) | 267 (0.20) | 165 (0.14) |
|  | $C_2H_4$ | 106 (0.08) | 78 (0.06) | 75 (0.05) | N/A |
|  | $C_2H_2$ | N/A | N/A | N/A | N/A |
|  | $C_3H_8$ | 387 (0.08) | 233 (0.17) | 180 (0.13) | 71 (0.06) |
|  | $C_3H_6$ | 36 (0.03) | 24 (0.02) | 26 (0.02) | N/A |
|  | $C_4H_{10}$ | 113 (0.08) | 73 (0.05) | 71 (0.05) | 28 (0.02) |
|  | $C_5H_{12}$ | 45 (0.03) | 17 (0.01) | 16 (0.01) | 14 (0.01) |

As shown in Table 2, the photocatalysts of Example 1 to Example 20 of the present disclosure can reduce the carbon dioxide by the photocatalytic reaction, and manufacture the multi-carbon hydrocarbon compounds by the separation and purification process, and the obtained hydrocarbon compounds all have the excellent yields.

In conclusion, the method for reducing carbon dioxide to manufacture the multi-carbon hydrocarbon compound of the present disclosure is based on the designed reduction reaction with separation and purification system, the carbon dioxide is reduced by the photocatalyst to form the various products, and the multi-carbon hydrocarbon compound is manufactured by using the different properties of the products to perform the separation and the purification. Furthermore, the carbon dioxide can be recovered to form the carbon cycle to achieve the goal of the sustainable development.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:
1. A method for reducing carbon dioxide to manufacture a multi-carbon hydrocarbon compound, comprising:
   providing a reduction reaction with separation and purification system, comprising:
      a carbon dioxide absorption tower having an absorbent;
      a reactor communicated to a liquid outlet of the carbon dioxide absorption tower and having a photocatalyst;
      a gas-liquid separation device communicated with the reactor, and the gas-liquid separation device connected with a liquid-phase tank and a gas-phase tank by a first flow path and a second flow path, respectively;

a liquid-phase purification device communicated with the liquid-phase tank; and a gas-phase purification device comprising a washing tower and at least one separation column set, wherein the washing tower is communicated with the gas-phase tank, and the at least one separation column set is connected with the washing tower;

performing an absorption step, wherein a carbon dioxide gas is performed a carbon dioxide absorption treatment by the absorbent in the carbon dioxide absorption tower to form a mixed solution;

performing a photocatalysis step, wherein the mixed solution is reacted with the photocatalyst under an irradiation of a light source in the reactor to form a carbon-based compound;

performing a separation step, wherein the carbon-based compound is separated by the gas-liquid separation device to form a liquid-phase mixture and a gas-phase mixture, which are stored in the liquid-phase tank and the gas-phase tank, respectively;

performing a liquid-phase purification step, wherein the liquid-phase mixture is filtered and dried in the liquid-phase purification device to purify the liquid-phase mixture; and performing a gas-phase purification step, wherein the gas-phase mixture is washed by the washing tower, and separated and purified the gas-phase mixture in the at least one separation column set by a pressure swing adsorption method in the gas-phase purification device to form a multi-carbon hydrocarbon compound.

2. The method for reducing carbon dioxide to manufacture the multi-carbon hydrocarbon compound of claim 1, wherein the absorbent is a sodium hydroxide.

3. The method for reducing carbon dioxide to manufacture the multi-carbon hydrocarbon compound of claim 1, wherein the photocatalyst comprises a selenium-based compound, a tellurium-based compound, an arsenic-based compound or a compound represented by formula (i), formula (ii), formula (iii), formula (iv) or formula (v):

| | |
|---|---|
| $M^1A^1X$ | formula (i), |
| $M^2BiO_2X$ | formula (ii), |
| $BiOX/BiOY$ | formula (iii), |
| $BiOX/BiOY/BiOZ$ | formula (iv), |
| $M^3A^2O$ | formula (v); | wherein $M^1$ is bismuth, antimony, gallium or indium, $M^2$ is lead, calcium, strontium, barium, copper or iron, and $M^3$ is lithium, sodium, or potassium;

wherein $A^1$ is oxygen, sulfur, selenium or tellurium, and $A^2$ is titanium, vanadium, chromium, manganese, iron, cobalt, nickel, zirconium, niobium, tantalum, molybdenum or tungsten;

wherein X, Y, Z are fluorine, chlorine, bromine or iodine.

4. The method for reducing carbon dioxide to manufacture the multi-carbon hydrocarbon compound of claim 3, wherein the photocatalyst further comprises a composite of the selenium-based compound, the tellurium-based compound, the arsenic-based compound or the compound represented by formula (i), formula (ii), formula (iii), formula (iv) or formula (v) with a two-dimensional structural material.

5. The method for reducing carbon dioxide to manufacture the multi-carbon hydrocarbon compound of claim 4, wherein the two-dimensional structure material is a graphitic carbon nitride, a graphene oxide, a bismuth oxyhalide-based compound, a sulfur-doped graphitic carbon nitride, a carbon nanotube or a graphene.

6. The method for reducing carbon dioxide to manufacture the multi-carbon hydrocarbon compound of claim 1, wherein a number of the at least one separation column set is three.

7. The method for reducing carbon dioxide to manufacture the multi-carbon hydrocarbon compound of claim 1, wherein an adsorbent material contained in the at least one separation column set is a zeolite, a silica gel, an activated carbon, an activated oxidation aluminum or a 4 Å molecular sieve.

8. The method for reducing carbon dioxide to manufacture the multi-carbon hydrocarbon compound of claim 1, wherein the at least one separation column set comprises an adsorption column and a desorption column.

9. The method for reducing carbon dioxide to manufacture the multi-carbon hydrocarbon compound of claim 1, further comprising a detection step, wherein a detection device is connected to the gas-phase purification device to measure a production of the multi-carbon hydrocarbon compound.

10. The method for reducing carbon dioxide to manufacture the multi-carbon hydrocarbon compound of claim 9, wherein the detection device is a gas chromatography.

* * * * *